US012576069B2

(12) United States Patent
Nassiri et al.

(10) Patent No.: US 12,576,069 B2
(45) Date of Patent: Mar. 17, 2026

(54) COMPOSITIONS AND METHODS FOR TREATING SLOW-FLOW VASCULAR MALFORMATIONS

(71) Applicant: YALE UNIVERSITY, New Haven, CT (US)

(72) Inventors: Naiem Nassiri, New Haven, CT (US); Prashant Patel, Cheshire, CT (US)

(73) Assignee: Yale University, New Haven, CT (US)

( * ) Notice: Subject to any disclaimer, the term of this patent is extended or adjusted under 35 U.S.C. 154(b) by 1042 days.

(21) Appl. No.: 17/642,138

(22) PCT Filed: Sep. 10, 2020

(86) PCT No.: PCT/US2020/050223
§ 371 (c)(1),
(2) Date: Mar. 10, 2022

(87) PCT Pub. No.: WO2021/050743
PCT Pub. Date: Mar. 18, 2021

(65) Prior Publication Data
US 2022/0378754 A1      Dec. 1, 2022

Related U.S. Application Data

(60) Provisional application No. 62/898,937, filed on Sep. 11, 2019.

(51) Int. Cl.
| | |
|---|---|
| *A61K 31/436* | (2006.01) |
| *A61K 9/08* | (2006.01) |
| *A61K 31/675* | (2006.01) |
| *A61P 9/14* | (2006.01) |

(52) U.S. Cl.
CPC .............. *A61K 31/436* (2013.01); *A61K 9/08* (2013.01); *A61K 31/675* (2013.01); *A61P 9/14* (2018.01)

(58) Field of Classification Search
CPC .................................................... A61K 31/436
See application file for complete search history.

(56) References Cited

U.S. PATENT DOCUMENTS

| | | | |
|---|---|---|---|
| 9,175,011 B2 | 11/2015 | Lynch et al. | |
| 10,004,803 B2 | 6/2018 | Mannick et al. | |
| 2003/0170287 A1* | 9/2003 | Prescott ................. | A61P 43/00 |
| | | | 604/500 |
| 2010/0233236 A1* | 9/2010 | Zhao ................... | A61K 31/4745 |
| | | | 427/2.25 |
| 2013/0059009 A1 | 3/2013 | Kishimoto et al. | |
| 2018/0015075 A1 | 1/2018 | Boscolo et al. | |
| 2018/0117055 A1 | 5/2018 | Baselga et al. | |
| 2018/0193320 A1 | 7/2018 | Kaupinen et al. | |

FOREIGN PATENT DOCUMENTS

| | | |
|---|---|---|
| WO | 2010005726 A2 | 1/2010 |
| WO | 2020041329 A1 | 2/2020 |

OTHER PUBLICATIONS

"International Search Report and Written Opinion issued by the International Searching Authority (US) on Dec. 4, 2020, for Intl. Appl. No. PCT/US2020/050223", 10 pages.

* cited by examiner

*Primary Examiner* — Rei Tsang Shiao
(74) *Attorney, Agent, or Firm* — Saul Ewing, LLP; Domingos Silva; Kathryn Doyle

(57)      ABSTRACT

The disclosure relates in part to the discovery that slow-flow vascular malformations (which can be venous and/or lymphatic) can be treated using direct intralesional delivery of an active drug, such as but not limited to a mTOR inhibitor, such as but not limited to temsirolimus, or a salt or solvate thereof.

17 Claims, 9 Drawing Sheets

COMPOSITIONS AND METHODS FOR TREATING SLOW-FLOW VASCULAR MALFORMATIONS

CROSS-REFERENCE TO RELATED APPLICATIONS

The present application is a 35 U.S.C. § 371 national phase application of, and claims priority to, International Application No. PCT/US2020/050223 filed Sep. 10, 2020, which claims priority under 35 U.S.C. § 119(e) to U.S. Provisional Application No. 62/898,937 filed Sep. 11, 2019, which applications are hereby incorporated herein by reference in their entireties.

BACKGROUND

Vascular malformations encompass a wide clinical spectrum, ranging from lesions of cosmetic concern to life- or limb-threatening conditions. Each subtype represents a distinct clinical entity with idiosyncratic angio-architecture, hemodynamics, and natural history. Within each subtype, the anatomic distribution, extent of the lesion, and association with known genetic mutations and affiliated syndromes can further alter the clinical course and affect overall prognosis.

No cure or standardized therapeutic modality currently exists for congenital vascular malformations. Treatment has remained a challenging clinical problem despite multidisciplinary efforts and commonly employed, off-label, non-standardized surgical, and interventional techniques for local control. Despite these widespread efforts, many lesions (up to 80%) remain refractory to these conventional methods. Repeat sessions of treatment is the norm rather than the exception for the vast majority of these lesions, and the side effect profile—particularly for some of the more potent and toxic therapeutic agents such as absolute ethanol—can be high (up to 50%) and, at times, lethal.

Venous and lymphatic malformations are considered slow-flow vascular malformations as they lack direct arterial connections and do not contain a fast-flow, highly pressurized, arterialized shunt. For these slow-flow lesions, current first-line therapy is direct stick embolization or direct intralesional delivery of chemicals that aim to plug, thrombose, or irritate the lesion enough to cause symptom relief. Typical chemicals used in those cases include absolute ethanol (a toxic sclerosant that denatures proteins and destroys the blood vessel), sodium tetradecyl sulfate or STS (an anionic surfactant that acts as a detergent-like compound binding the endothelial cells and causing an inflammatory reaction), n-butyl cyanoacrylate (a rapidly polymerizing adhesive), and doxycycline (an antibiotic agent used for its anti-VEGF and anti-MMP properties). All these agents are used off-label without formal FDA-approval for malformation treatment.

The direct intralesional delivery procedure is performed in the hybrid operating room or interventional suite under sterile conditions. The technique involves ultrasound-guided or blind percutaneous puncture of the malformation with a needle or a needle sheath combination. This is followed by direct infusion of radiopaque dye into the malformation under fluoroscopy in order to outline the extent of the accessed portion of the malformation and to confirm intraluminal/intralesional position of the needle tip. Following this, the chemical of choice (often mixed with contrast or with an oily contrast medium such as lipiodol) is injected through the needle into the malformation. The needle is then withdrawn and the access tract is plugged. While this route of delivery is highly precise and focal, none of the currently employed chemicals address the etiological molecular pathways implicated in the pathogenesis of the targeted lesion.

Thanks to advancements in DNA sequencing, the understanding of the etiological mutagenic pathways involved in the pathogenesis of vascular malformations has expanded drastically in recent years. It is now known that slow-flow venous and lymphatic malformations and associated syndromes (such as Klippel-Trenaunay, CLOVES, and Proteus Syndromes) feature somatic mosaic mutations in the mTOR cell-signaling pathway with specific mutations involving PIK3CA, AKT, TIE II, and so forth, depending on the clinical subtype and the phenotype manifested.

As such, there has been a growing interest in off-label or experimental use of the currently available mTOR pathway inhibitor rapamycin (sirolimus) for treatment of slow-flow vascular malformations and associated syndromes. Non-focal, systemic, oral administration of sirolimus has been used in a phase II clinical trial enrolling 61 patients. 57 patients were treated with 6 or more courses (each course was 28 days each) of continuous dosing schedule of oral rapamycin, starting at 0.8 $mg/m^2$ per dose twice daily, to achieve serum concentration levels of 10 to 15 ng/mL. 47 patients had a partial response, 3 patients had stable disease, and 7 patients had progressive disease at the end of their sixth course. Two patients were taken off of the study due to persistent adverse effects. Grade 3 and higher toxicities attributable to rapamycin included blood/bone marrow toxicity in 27% of patients, gastrointestinal toxicity in 3%, and metabolic/laboratory toxicity in 3%. Other commonly reported negative side effects of rapamycin have included stomatitis, headache, infections, myelodepression, acne, and hyperlipidemia.

While this trial showed that rapamycin can be an efficacious treatment for the majority of patients with complicated vascular malformations, the study also demonstrated that regular daily dosing with frequent blood level checks are required and the side-effect profile associated with non-localized systemic oral delivery is considerable and can limit treatment delivery.

There is still a need in the art for a therapeutic treatment of congenital vascular malformations that is effective and has manageable (or negligible) side effects. The present disclosure addresses and meets this need.

BRIEF SUMMARY OF THE DISCLOSURE

The disclosure provides in one aspect a sterile dose unit of a mTOR inhibitor, wherein the mTOR is in a solution, or can be dissolved in a solvent to form a solution, and wherein the mTOR inhibitor concentration in the solution ranges from about 0.5 mg/ml to about 5 mg/ml.

The disclosure provides in another aspect a method of treating at least one of a congenital vascular malformation, Klippel-Trenaunay syndrome, CLOVES syndrome, and Proteus syndrome in a subject. In certain embodiments, the method comprises intralesionally administering to the subject a therapeutically effective amount of a mTOR inhibitor.

BRIEF DESCRIPTION OF THE DRAWINGS

For the purpose of illustrating the disclosure, certain embodiments of the disclosure are depicted in the drawings. However, the disclosure is not limited to the precise arrangements and instrumentalities of the embodiments depicted in the drawings.

FIG. 6A: Under ultrasound guidance, needle puncture and intraluminal access of the nasal venous malformation was achieved. FIG. 6B: A 1 mg/mL solution of Temsirolimus (25 mg/1 mL of Temsirolimus in 1.8 mL prepackaged diluent, 2 mL Omnipaque, and ~20-22.5 mL Normal Saline) was agitated in preparation for direct intraluminal injection. FIG. 6C: The solution was injected intraluminally into the venous malformation under direct fluoroscopic guidance. The addition of contrast allowed for monitoring of the extent of solution spread into the malformation.

DETAILED DESCRIPTION OF THE DISCLOSURE

Figure 1:
FIG. 1 illustrates images of typical venous malformations on the body as well as in contrast enhanced magnetic resonance imaging (MRI).
Figure 1:
Figure 1:

The disclosure relates in part to the unexpected discovery that slow-flow vascular malformations (which can be venous and/or lymphatic) can be treated or prevented using direct intralesional delivery of an active drug, such as but not limited to a mTOR inhibitor, such as but not limited to temsirolimus, or a salt or solvate thereof.

Existing technology for direct intralesional treatment of slow-flow vascular malformations relies on non-molecularly active agents that aim to merely clot, plug, or irritate the affected blood vessels without affecting the underlying, etiological mechanism involved in the pathogenesis of the malformations. This etiological mechanism is now well-established to be the mTOR pathway for the slow-flow vascular malformations. While systemic oral delivery of the mTOR pathway inhibitor rapamycin has shown >80% response rate, direct, intralesional, focal delivery of a sterile, intravenous formulation of an mTOR inhibitor (such as temsirolimus) has never been attempted previously.

In certain embodiments, the drug contemplated in the disclosure addresses the etiological pathogenic mechanism directly at the site of the mutated endothelial cells (rather than merely irritating or plugging the diseased blood vessels). In certain embodiments, the drug contemplated in the disclosure is compatible for intravenous delivery. In certain embodiments, the drug contemplated in the disclosure can be injected under sterile surgical environments. In certain embodiments, the drug contemplated in the disclosure is the only molecularly active therapeutic agent administered intralesionally into slow-flow vascular malformations. In certain embodiments, the drug contemplated in the disclosure is diluted and radio-opacified to facilitate direct intralesional delivery under fluoroscopic guidance. In certain embodiments, the drug contemplated in the disclosure can be delivered repeatedly under sterile conditions.

In certain embodiments, the methods contemplated in the disclosure forego need for non-localized, systemic delivery, thereby minimizing the drug dose and/or drug side effects and/or drug toxicity. In certain embodiments, the methods contemplated in the disclosure minimize stomatitis associated with systemic administration of the drug. In certain embodiments, the methods contemplated in the disclosure minimize headache associated with systemic administration of the drug. In certain embodiments, the methods contemplated in the disclosure minimize infections associated with systemic administration of the drug. In certain embodiments, the methods contemplated in the disclosure minimize myelodepression associated with systemic administration of the drug. In certain embodiments, the methods contemplated in the disclosure minimize blood/bone marrow toxicity associated with systemic administration of the drug. In certain embodiments, the methods contemplated in the disclosure minimize gastrointestinal toxicity associated with systemic administration of the drug. In certain embodiments, the methods contemplated in the disclosure minimize metabolic/laboratory toxicity associated with systemic administration of the drug. In certain embodiments, the methods contemplated in the disclosure minimize acne associated with systemic administration of the drug. In certain embodiments, the methods contemplated in the disclosure minimize hyperlipidemia associated with systemic administration of the drug.

The non-localized, systemic, oral delivery of rapamycin requires continuous BID dosing to achieve a serum concentration that is necessary to exert an effect on relatively focal lesions. As such, total delivered dose and side effect risks are higher with this route of delivery. As described herein, a much more precise, localized, and focal mTOR inhibitor drug delivery using the aforementioned direct intralesional delivery technique overcomes the limitation of systemic delivery of mTOR inhibitors. Further, the present disclosure provides IV formulation of sirolimus (also known as rapamycin) and/or temsirolimus (which is a pro-drug of sirolimus).

Sirolimus is currently pharmacologically available solely as an oral solution in a non-sterile formulation. Direct intralesional delivery of this solution would require sterilization—a process for which no standardized validation mechanism exists. Furthermore, sirolimus is insoluble in water, and organic diluents (such as alcohols) required for its dissolution are not readily available, are non-sterile, and difficult to sterilize (because of their volatilely and/or flammability). In fact, there is no published literature for preparing sterilized solutions of sirolimus for pharmacological use, and it is unclear what the pH and tonicity of the final sterilized product should be for pharmacological use.

Temsirolimus is currently FDA-approved for treatment of renal cell carcinoma: it is delivered IV via weekly infusions of a 25 mg dose. Temsirolimus is "rapidly/readily" metabolized to sirolimus within 15 min of administration. In humans about 90% of temsirolimus in plasma is converted to sirolimus. Following a single 25 mg intravenous dose in patients with cancer, sirolimus AUC (drug exposure/pharmacodynamics activity) was 2.7-fold that of temsirolimus AUC. That is, even upon administration of temsirolimus, the AUC of sirolimus is greater in theoretical pharmacokinetic comparison of equal units intravenous sirolimus and temsirolimus. Upon IV infusion, temsirolimus has pharmacological activity of its own, and is then rapidly converted to sirolimus, which has further (major/prolonged) pharmacological activity. As a consequence, the peak concentration Cmax (safety) for both is almost similar. Given these circumstances, 1:1 dose equivalence is reasonable; and temsirolimus is a viable, intravenous-compatible, and sterile formulation that can be used to treat or prevent congenital vascular malformations.

The present disclosure includes pharmaceutical compositions comprising at least one pharmaceutically acceptable carrier and one or more pharmaceutically active agents contemplated herein. The pharmaceutical compositions described herein may be prepared by any method known or hereafter developed in the art of pharmacology. In general, such preparatory methods include bringing the active ingredient into association with a carrier or one or more other accessory ingredients, and then, if necessary or desirable, shaping or packaging the product into a desired single- or multi-dose unit.

In one aspect, the present disclosure provides dose units of an mTOR inhibitor, such as but not limited to temsirolimus. In certain embodiments, the dose unit has a mTOR inhibitor concentration ranging from about 0.5 mg/ml to about 5 mg/ml. In certain embodiments, the dose unit has a mTOR inhibitor concentration of about 1 mg/ml. In certain embodiments, the dose unit of the mTOR inhibitor is sterile. In certain embodiments, the dose unit of the mTOR inhibitor is formulated in a solution comprising a diluent, normal saline, and a radiopaque contrast dye and/or oily contrast media such as lipiodol. In certain embodiments, the dose unit of the mTOR inhibitor is formulated as a solution with total volume ranging from about 5 ml to about 25 ml. In certain embodiments, the dose unit of the mTOR inhibitor is formulated as a solution with total volume of about 10 ml.

The disclosure should not be construed to be limited to temsirolimus and/or sirolimus as the mTOR inhibitor. In fact, any mTOR inhibitor is useful within the methods of the disclosure.

In certain embodiments, the mTOR inhibitor is BEZ235, or a salt, solvate, enantiomer or diastereoisomer thereof. In certain embodiments, the mTOR inhibitor is rapamycin, or a salt, solvate, enantiomer or diastereoisomer thereof. In certain embodiments, the mTOR inhibitor is everolimus, or a salt, solvate, enantiomer or diastereoisomer thereof. In certain embodiments, the mTOR inhibitor is AZD8055, or a salt, solvate, enantiomer or diastereoisomer thereof. In certain embodiments, the mTOR inhibitor is Temsirolimus, or a salt, solvate, enantiomer or diastereoisomer thereof. In certain embodiments, the mTOR inhibitor is KU-0063794, or a salt, solvate, enantiomer or diastereoisomer thereof. In certain embodiments, the mTOR inhibitor is PI-103, or a salt, solvate, enantiomer or diastereoisomer thereof. In certain embodiments, the mTOR inhibitor is Torkinib, or a salt, solvate, enantiomer or diastereoisomer thereof. In certain embodiments, the mTOR inhibitor is Tacrolimus, or a salt, solvate, enantiomer or diastereoisomer thereof. In certain embodiments, the mTOR inhibitor is Ridaforolimus, or a salt, solvate, enantiomer or diastereoisomer thereof. In certain embodiments, the mTOR inhibitor is INK-128, or a salt, solvate, enantiomer or diastereoisomer thereof. In certain embodiments, the mTOR inhibitor is Voxtalisib, or a salt, solvate, enantiomer or diastereoisomer thereof. In certain embodiments, the mTOR inhibitor is Torin-1, or a salt, solvate, enantiomer or diastereoisomer thereof. In certain embodiments, the mTOR inhibitor is Omipalisib, or a salt, solvate, enantiomer or diastereoisomer thereof. In certain embodiments, the mTOR inhibitor is OSI-027, or a salt, solvate, enantiomer or diastereoisomer thereof. In certain embodiments, the mTOR inhibitor is PF-04691502, or a salt, solvate, enantiomer or diastereoisomer thereof. In certain embodiments, the mTOR inhibitor is Apitolisib, or a salt, solvate, enantiomer or diastereoisomer thereof. In certain embodiments, the mTOR inhibitor is GSK1059615, or a salt, solvate, enantiomer or diastereoisomer thereof. In certain embodiments, the mTOR inhibitor is WYE-354, or a salt, solvate, enantiomer or diastereoisomer thereof. In certain embodiments, the mTOR inhibitor is Gedatolisib, or a salt, solvate, enantiomer or diastereoisomer thereof. In certain embodiments, the mTOR inhibitor is AZD-2014, or a salt, solvate, enantiomer or diastereoisomer thereof. In certain embodiments, the mTOR inhibitor is Torin-2, or a salt, solvate, enantiomer or diastereoisomer thereof. In certain embodiments, the mTOR inhibitor is WYE-125132, or a salt, solvate, enantiomer or diastereoisomer thereof. In certain embodiments, the mTOR inhibitor is BGT226, or a salt, solvate, enantiomer or diastereoisomer thereof. In certain embodiments, the mTOR inhibitor is Palomid-529, or a salt, solvate, enantiomer or diastereoisomer thereof. In certain embodiments, the mTOR inhibitor is PP121, or a salt, solvate, enantiomer or diastereoisomer thereof. In certain embodiments, the mTOR inhibitor is WYE-687, or a salt, solvate, enantiomer or diastereoisomer thereof. In certain embodiments, the mTOR inhibitor is CH5132799, or a salt, solvate, enantiomer or diastereoisomer thereof. In certain embodiments, the mTOR inhibitor is Way-600, or a salt, solvate, enantiomer or diastereoisomer thereof. In certain embodiments, the mTOR inhibitor is ETP-46464, or a salt, solvate, enantiomer or diastereoisomer thereof. In certain embodiments, the mTOR inhibitor is GDC-0349, or a salt, solvate, enantiomer or diastereoisomer thereof. In certain embodiments, the mTOR inhibitor is XL388, or a salt, solvate, enantiomer or diastereoisomer thereof. In certain embodiments, the mTOR inhibitor is Zotarolimus, or a salt, solvate, enantiomer or diastereoisomer thereof. In other embodiments, the mTOR inhibitor is at least one selected from the group consisting of rapamycin, Ridaforolimus, and Everolimus, or a salt, solvate, enantiomer or diastereoisomer thereof. In yet other embodiments, the mTOR inhibitor is rapamycin, or a salt, solvate, enantiomer or diastereoisomer thereof.

In certain embodiments, the mTOR inhibitor is not BEZ235, or a salt, solvate, enantiomer or diastereoisomer thereof. In certain embodiments, the mTOR inhibitor is not rapamycin, or a salt, solvate, enantiomer or diastereoisomer thereof. In certain embodiments, the mTOR inhibitor is not everolimus, or a salt, solvate, enantiomer or diastereoisomer thereof. In certain embodiments, the mTOR inhibitor is not AZD8055, or a salt, solvate, enantiomer or diastereoisomer thereof. In certain embodiments, the mTOR inhibitor is not Temsirolimus, or a salt, solvate, enantiomer or diastereoisomer thereof. In certain embodiments, the mTOR inhibitor is not KU-0063794, or a salt, solvate, enantiomer or diastereoisomer thereof. In certain embodiments, the mTOR inhibitor is not PI-103, or a salt, solvate, enantiomer or diastereoisomer thereof. In certain embodiments, the mTOR inhibitor is not Torkinib, or a salt, solvate, enantiomer or diastereoisomer thereof. In certain embodiments, the mTOR inhibitor is not Tacrolimus, or a salt, solvate, enantiomer or diastereoisomer thereof. In certain embodiments, the mTOR inhibitor is not Ridaforolimus, or a salt, solvate, enantiomer or diastereoisomer thereof. In certain embodiments, the mTOR inhibitor is not INK-128, or a salt, solvate, enantiomer or diastereoisomer thereof. In certain embodiments, the mTOR inhibitor is not Voxtalisib, or a salt, solvate, enantiomer or diastereoisomer thereof. In certain embodiments, the mTOR inhibitor is not Torin-1, or a salt, solvate, enantiomer or diastereoisomer thereof. In certain embodiments, the mTOR inhibitor is not Omipalisib, or a salt, solvate, enantiomer or diastereoisomer thereof. In certain embodiments, the mTOR inhibitor is not OSI-027, or a salt, solvate, enantiomer or diastereoisomer thereof. In certain embodiments, the mTOR inhibitor is not PF-04691502, or a salt, solvate, enantiomer or diastereoisomer thereof. In certain embodiments, the mTOR inhibitor is not Apitolisib, or a salt, solvate, enantiomer or diastereoisomer thereof. In certain embodiments, the mTOR inhibitor is not GSK1059615, or a salt, solvate, enantiomer or diastereoisomer thereof. In certain embodiments, the mTOR inhibitor is not WYE-354, or a salt, solvate, enantiomer or diastereoisomer thereof. In certain embodiments, the mTOR inhibitor is not Gedatolisib, or a salt, solvate, enantiomer or diastereoisomer thereof. In certain embodiments, the mTOR inhibitor is not AZD-2014, or a salt, solvate, enantiomer or diastereoisomer thereof. In certain embodiments, the mTOR inhibitor is not Torin-2, or a salt, solvate, enantiomer or diastereoisomer thereof. In certain embodiments, the mTOR inhibitor is not WYE-125132, or a salt, solvate, enantiomer or diastereoisomer thereof. In certain embodiments, the mTOR inhibitor is not BGT226, or a salt, solvate, enantiomer or diastereoisomer thereof. In certain embodiments, the mTOR inhibitor is not Palomid-529, or a salt, solvate, enantiomer or diastereoisomer thereof. In certain embodiments, the mTOR inhibitor is not PP121, or a salt, solvate, enantiomer or diastereoisomer thereof. In certain embodiments, the mTOR inhibitor is not WYE-687, or a salt, solvate, enantiomer or diastereoisomer thereof. In certain embodiments, the mTOR inhibitor is not CH5132799, or a salt, solvate, enantiomer or diastereoisomer thereof. In certain embodiments, the mTOR inhibitor is not Way-600, or a salt, solvate, enantiomer or diastereoisomer thereof. In certain embodiments, the mTOR inhibitor is not ETP-46464, or a salt, solvate, enantiomer or diastereoisomer thereof. In certain embodiments, the mTOR inhibitor is not GDC-0349, or a salt, solvate, enantiomer or diastereoisomer thereof. In certain embodiments, the mTOR inhibitor is not XL388, or a salt, solvate, enantiomer or diastereoisomer thereof. In certain embodiments, the mTOR inhibitor is not Zotarolimus, or a salt, solvate, enantiomer or diastereoisomer thereof.

The compounds of the disclosure may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereomers or mixtures thereof.

In certain embodiments, the compounds of the disclosure exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein can form salts with acids and/or bases, and such salts are included in the present disclosure. In certain embodiments, the salts are pharmaceutically acceptable salts. The term "salts" embraces addition salts of free acids and/or bases that are useful within the methods of the disclosure. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present disclosure, such as for example utility in process of synthesis, purification or formulation of compounds useful within the methods of the disclosure.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the disclosure include, for example, ammonium salts, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (also known as N-methylglucamine) and procaine. All of these salts may be prepared from the corresponding compound by reacting, for example, the appropriate acid or base with the compound.

Definitions

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, illustrative methods and materials are described. As used herein, each of the following terms has the meaning associated with it in this section.

Generally, the nomenclature used herein and the laboratory procedures in medicine, pharmacology. and organic chemistry are those well-known and commonly employed in the art.

Standard techniques are used for biochemical and/or biological manipulations. The techniques and procedures are generally performed according to conventional methods in the art and various general references (e.g., Sambrook & Russell, 2012, Molecular Cloning, A Laboratory Approach, Cold Spring Harbor Press, Cold Spring Harbor, NY, and Ausubel, et al., 2002, Current Protocols in Molecular Biology, John Wiley & Sons, NY), which are provided throughout this document.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A disease or disorder is "alleviated" if the severity or frequency of at least one sign or symptom of the disease or disorder experienced by a patient is reduced.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" or "therapeutically effective amount" of a compound or composition is that amount of compound or composition that is sufficient to provide a beneficial effect to the subject to which the compound or composition is administered. An "effective amount" of a delivery vehicle is that amount sufficient to effectively bind or deliver a compound or composition.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

"Naturally occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or composition useful within the disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound or composition useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound or composition useful within the disclosure, and are physiologically acceptable to the patient. Supplementary active compounds may also be incorporated into the compositions. The "pharmaceutically acceptable carrier" may further include a pharmaceutically acceptable salt of the compound useful within the disclosure. Other additional ingredients that may be included in the pharmaceutical compositions used in the practice of the disclosure are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" or "therapeutically acceptable salt" refers to a salt of the administered compounds prepared from pharmaceutically acceptable non-toxic acids, including inorganic acids or bases, organic acids or bases, solvates, hydrates, or clathrates thereof.

The terms "pharmaceutically effective amount" and "effective amount" or "therapeutically effective amount" refer to a nontoxic but sufficient amount of an agent to provide the desired biological result. That result can be reduction and/or alleviation of the signs, symptoms, or causes of a disease or disorder, or any other desired alteration of a biological system. The amount of a compound of the disclosure that constitutes a "therapeutically effective amount" varies depending on the compound, the disease state and its severity, the age of the patient to be treated, and the like. An appropriate effective amount in any individual case may be determined by one of ordinary skill in the art using routine experimentation.

As used herein, the terms "polypeptide," "protein" and "peptide" are used interchangeably and refer to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

A "therapeutic" treatment is a treatment administered to a subject who exhibits signs of pathology, for the purpose of diminishing or eliminating those signs.

The terms "treat," "treating" and "treatment," as used herein, means reducing the frequency or severity with which symptoms of a disease or condition are experienced by a subject by virtue of administering an agent or compound to the subject.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Methods

In one aspect, the present disclosure provides a method for treating at least one of a congenital vascular malformation, Klippel-Trenaunay syndrome, CLOVES syndrome, and Proteus syndrome.

In certain embodiments, the subject in need of such treatment is intralesionally administered a therapeutically effective amount of a mTOR inhibitor. In certain embodiments, the mTOR inhibitor is the only therapeutically effective agent administered to the subject to treat or prevent the congenital vascular malformation. In certain embodiments, the congenital vascular malformation is venous. In certain embodiments, the congenital vascular malformation is lymphatic. In certain embodiments, the mTOR inhibitor is administered as a dose unit described elsewhere herein. In certain embodiments, the subject is a mammal. In certain embodiments, the subject is human.

In certain embodiments, the subject is treated in a single surgical procedure under sterile conditions. The frequency and length of therapy depends on the patient's response to the treatment, as guided by the patient's report of symptom severity and/or imaging surveillance, such as but not limited to MRI and ultrasound. The procedure can be repeated as often as necessary, as determined by the treating physician. In certain embodiments, the treatment is not performed more frequently than once every month, for example.

In certain embodiments, the pharmaceutical compositions of the disclosure, or any of the active agents contemplated in the disclosure (separately and/or in combination), are administered to the subject in need thereof using any known and applicable route of administration, such as for example, intravenous and intralesional.

Administration/Dosage/Formulations

The regimen of administration may affect what constitutes an effective amount. The therapeutic formulations may be administered to the subject after the onset of a disease or disorder contemplated in the disclosure. Further, several divided dosages, as well as staggered dosages may be administered sequentially or the dose may be a single-session, bolus injection. Further, the dosages of the therapeutic formulations may be proportionally increased or decreased as indicated by the exigencies of the therapeutic or prophylactic situation.

Administration of the compositions of the present disclosure to a patient, preferably a mammal, more preferably a human, may be carried out using known procedures, at dosages and for periods of time effective to treat a disease or disorder contemplated in the disclosure. An effective amount of the therapeutic compound or composition necessary to achieve a therapeutic effect may vary according to factors such as the state of the disease or disorder in the patient; the age, sex, and weight of the patient; and the ability of the therapeutic compound to treat a disease or disorder contemplated in the disclosure. Dosage regimens may be adjusted to provide the optimum therapeutic response. For example, several divided doses may be administered annually or the dose may be proportionally reduced as indicated by the exigencies of the therapeutic situation. A non-limiting example of an effective dose range for a therapeutic compound of the disclosure is from about 1 and 5,000 mg/kg of body weight/per day. The pharmaceutical compositions useful for practicing the disclosure may be administered to deliver a dose of from 1 ng/kg/day and 100 mg/kg/day. One of ordinary skill in the art would be able to study the relevant factors and make the determination regarding the effective amount of the therapeutic compound without undue experimentation.

Actual dosage levels of the active ingredients in the pharmaceutical compositions of this disclosure may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician, having ordinary skill in the art may readily determine and prescribe the effective amount of the pharmaceutical composition required. For example, the physician could start doses of the compounds of the disclosure employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the disclosure are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated in the disclosure.

In one embodiment, the compositions of the disclosure are formulated using one or more pharmaceutically acceptable excipients or carriers. In one embodiment, the pharmaceutical compositions of the disclosure comprise a therapeutically effective amount of a compound of the disclosure and a pharmaceutically acceptable carrier. In certain embodiments, the compositions comprise polysorbate 80. In certain embodiments, the compositions comprise polyethylene glycol, such as but not limited to polyethylene glycol 400. In certain embodiments, the compositions comprise dehydrated alcohol.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the disclosure are administered to the patient in dosages that range from one to 12 times per year or more. In another embodiment, the compositions of the disclosure are administered to the patient in range of dosages that include, but are not limited to once a day, once a month, and once a year. It is readily apparent to one skilled in the art that the frequency of administration of the various combination compositions of the disclosure varies from individual to individual depending on many factors including, but not limited to, age, disease or disorder to be treated, gender, overall health, and other factors. Thus, the disclosure should not be construed to be limited to any particular dosage regime and the precise dosage and composition to be administered to any patient is determined by the attending physical taking all other factors about the patient into account.

Compounds of the disclosure for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the disclosure is from about 1 mg and about 2,500 mg. In some embodiments, a dose of a compound of the disclosure used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present disclosure is directed to a packaged pharmaceutical composition comprising a container holding a therapeutically effective amount of a compound of the disclosure, alone or in combination with a second pharmaceutical agent; and instructions for using the compound to treat, prevent, or reduce one or more symptoms of a disease or disorder contemplated in the disclosure.

Formulations may be employed in admixtures with conventional excipients, i.e., pharmaceutically acceptable organic or inorganic carrier substances suitable for any suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

Routes of administration of any of the compositions of the disclosure include parenteral. The compounds for use in the disclosure may be formulated for administration by any suitable route, such as for parenteral, for example, transdermal, intravesical, intrathecal, subcutaneous, intramuscular, intradermal, intra-arterial, and intravenous administration.

Suitable compositions and dosage forms include, for example, dispersions, suspensions, solutions, syrups, gels, dry powders, and the like. It should be understood that the formulations and compositions that would be useful in the present disclosure are not limited to the particular formulations and compositions that are described herein.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Additional Administration Forms

Additional dosage forms of this disclosure include dosage forms as described in U.S. Pat. Nos. 6,340,475; 6,488,962; 6,451,808; 5,972,389; 5,582,837; and 5,007,790. Additional dosage forms of this disclosure also include dosage forms as described in U.S. Patent Applications Nos. 20030147952; 20030104062; 20030104053; 20030044466; 20030039688; and 20020051820. Additional dosage forms of this disclosure also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present disclosure may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds for use the method of the disclosure may be administered in the form of microparticles, for example, by injection or in the form of wafers or discs by implantation.

In one embodiment of the disclosure, the compounds of the disclosure are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present disclosure depends on the age, sex and weight of the patient, the current medical condition of the patient and the progression of a disease or disorder contemplated in the disclosure. The skilled artisan is able to determine appropriate dosages depending on these and other factors.

A suitable dose of a compound of the present disclosure may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the disclosure is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In one embodiment, patients require intermittent treatment on a long-term basis upon any recurrence of symptoms and/or infection.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Combination Therapies

In certain embodiments, the compounds of the disclosure are useful in the methods of the disclosure in combination with at least one additional agent useful for treating or preventing a disease or disorder contemplated herein in a mammal in need thereof. This additional agent may comprise compounds identified herein or compounds, e.g., commercially available compounds, known to treat, prevent or reduce the symptoms of a disease or disorder contemplated herein.

A synergistic effect may be calculated, for example, using suitable methods such as, for example, the Sigmoid-Emax equation (Holford & Scheiner, 1981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Kits

The disclosure includes a kit comprising at least one composition of the disclosure, an applicator, and an instructional material for use thereof.

The instructional material included in the kit comprises instructions for preventing or treating a disease or disorder contemplated within the disclosure. The instructional material recites the amount of, and frequency with which, at least one composition of the disclosure should be administered to the mammal. In other embodiments, the kit further comprises at least one additional agent that prevents or treats the disease or disorder contemplated within the disclosure.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, and reducing/oxidizing agents, with art-recognized alternatives and using no more than routine experimentation, are within the scope of the present application.

The following examples further illustrate aspects of the present disclosure. However, they are in no way a limitation of the teachings or disclosure of the present disclosure as set forth herein.

EXPERIMENTAL EXAMPLES

The disclosure is further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Example 1

A relatively healthy female patient in her 30s with severely symptomatic venous malformations of the subcutaneous and intramuscular components of her thigh was treated according to methods of the disclosure. Her lesions were examined and diagnosis of the condition was made and confirmed based on duplex ultrasound and contrast enhanced MRI.

For this study, a sterile solution of Temsirolimus (25 mg/mL mixed with 1.8 mL of prepackaged diluent [polysorbate 80, polyethylene glycol 400, and dehydrated alcohol] is further diluted with ~22 mL of Normal Saline for a final concentration of 1 mg/mL [25 mg/25 mL]). Solutions were delivered to the patient using an operating suite using a sterile syringe. A total of 2 mL of omnipaque intravenous contrast was added into the mixture for radiopacity purposes under fluoroscopy and for in vivo visualization of the drug. Final concentration of the mixture was approximately 1 mg/mL This mixture was agitated via a three-way stopcock in the absence of air.

The venous malformations were accessed percutaneously, using ultrasound and x-ray guidance. Intraluminal placement of the access needle was verified upon return of blood and confirmed by intralesional venography demonstrating the angioarchitecture of the targeted venous malformation. The prepared Temsirolimus emulsion was administered through direct intralesional delivery directly into the accessed venous malformation. Good deposition into the lesion, with minimal escape into the systemic circulation, was observed.

Different components of this multi focal venous malformation were similarly targeted and treated. On average, 10-15 mL of Temsirolimus emulsion was deposited into each lesion with a maximum dose of 25 mg (25 mL) per session. Serial x-rays revealed sustained presence of the emulsion inside the lesions without escape.

Needle access tracts were plugged using a collagen matrix foam, and a sterile dressing was applied. The procedure was done under general endotracheal anesthesia, and the patient received postoperative anti-inflammatory and analgesic medications. The patient's post-operative labs were within expected, normal limits. The patient had no perioperative complications, and was discharged home in stable condition.

Figure 2:
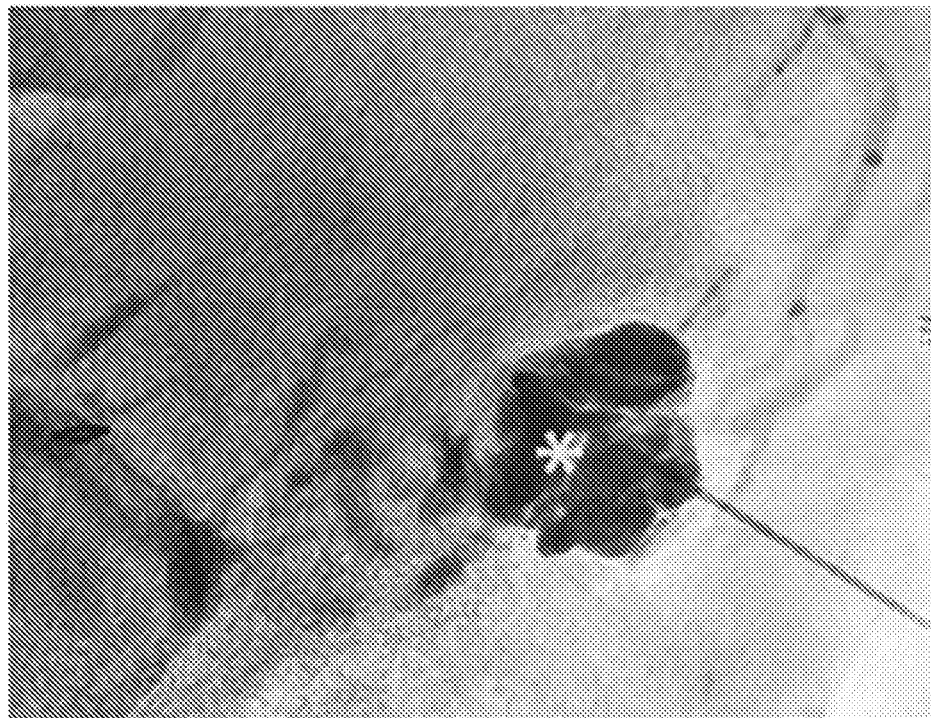
FIG. 2 illustrates a non-limiting intralesional delivery of a mTOR inhibitor under ultrasound and fluoroscopic guidance.
Figure 2:
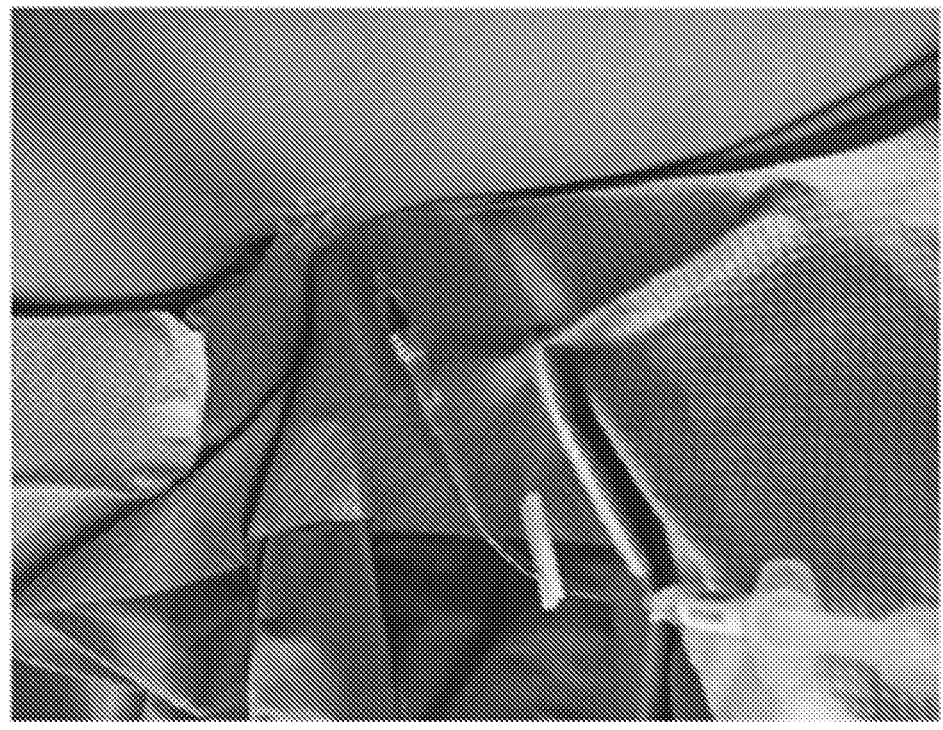
Figure 3:
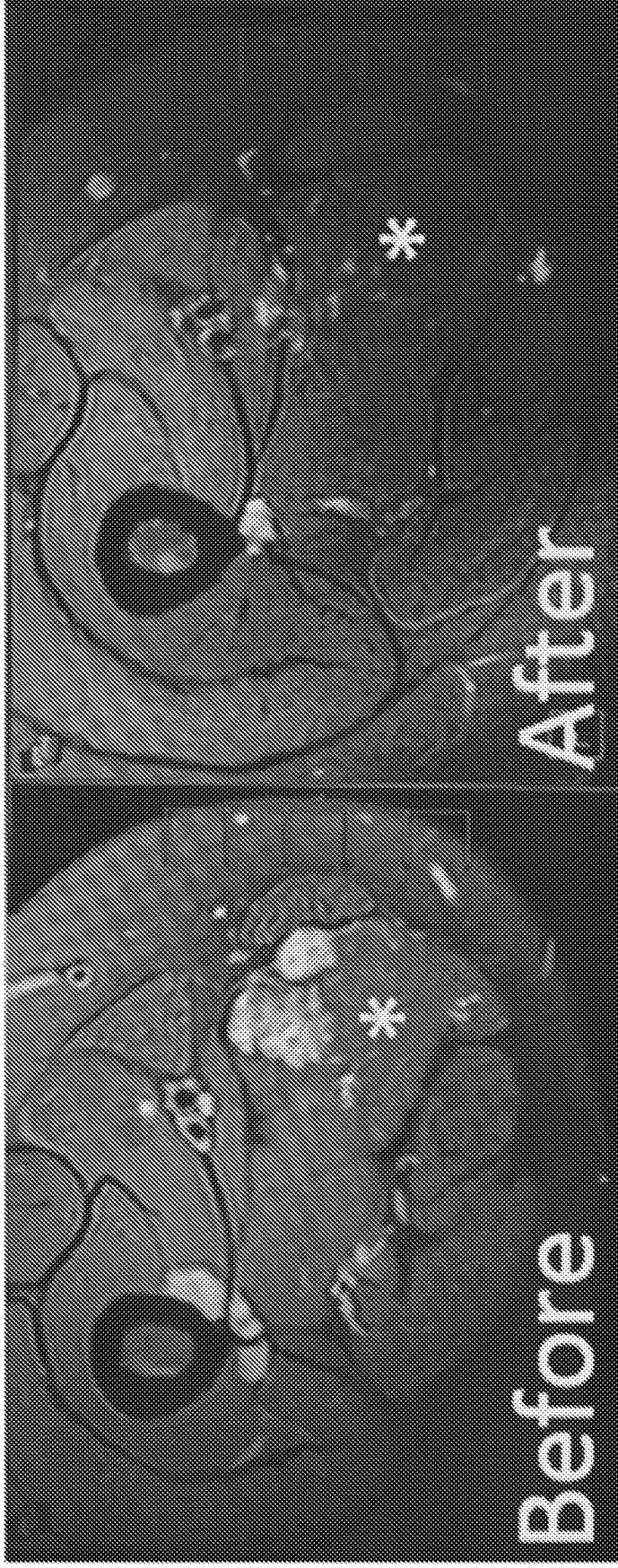
FIG. 3 illustrate magnetic resonance imagining (MRI) images obtained before and after embolization of a thigh venous malformation via an mTOR inhibitor. Administration of the mTOR inhibitor leads to lesion regression. The asterisks identify the same lesion in both images.
Figure 4:
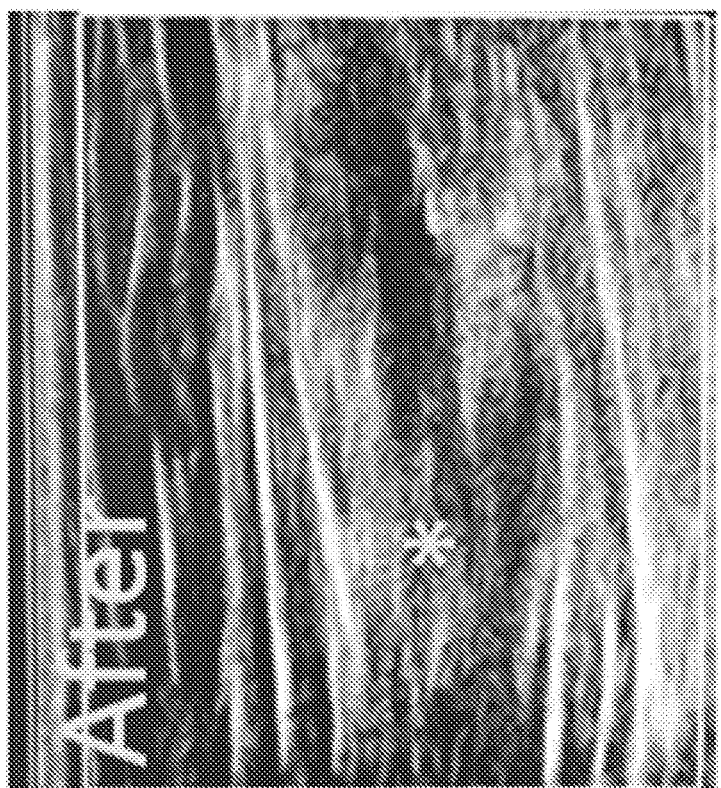
FIG. 4 illustrates color-flow Doppler images obtained before and after embolization of a venous malformation using an mTOR inhibitor. Administration of the mTOR inhibitor leads to flow cessation. The asterisks identify the same lesion in both images.
Figure 4:
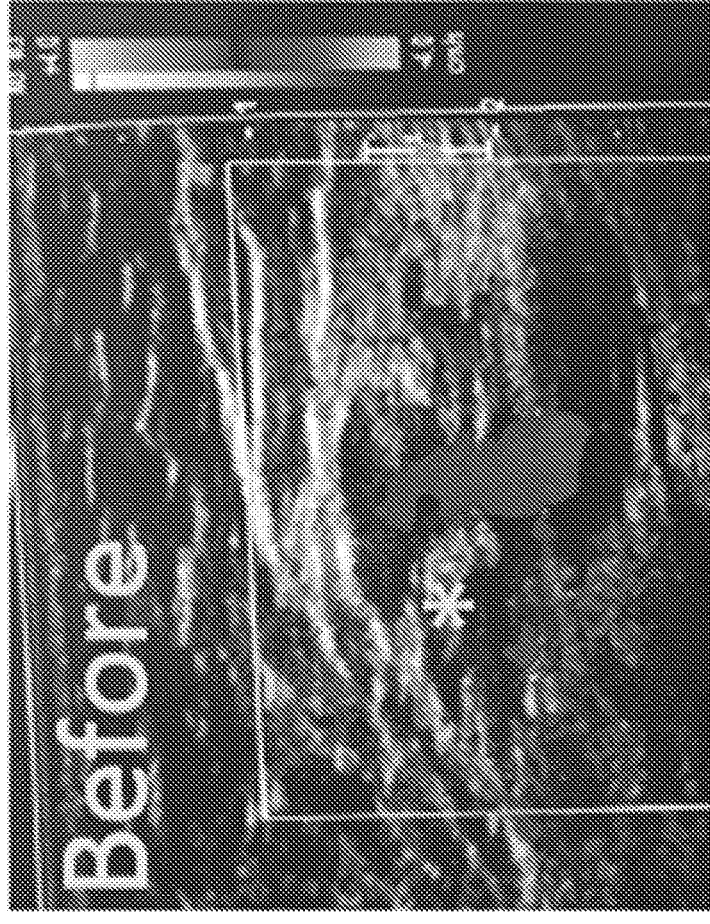

On a follow-up interviews on post-operative day two, 14, and 90, the patient expressed excellent pain relief, no evidence of fevers, infection FIG. 2 exemplifies selected photos intraoperatively documenting the procedure as outlined.

Example 2

A healthy male patient in his late 20s with a disfiguring, symptomatic venous malformation of the subcutaneous tissues of the left nare was treated according to methods of the disclosure. His lesion was examined, and diagnosis of the condition was made and confirmed based on contrast enhanced MRI.

For this study, a sterile solution of Temsirolimus (25 mg/mL mixed with 1.8 mL of prepackaged diluent [polysorbate 80, polyethylene glycol 400, and dehydrated alcohol] is further diluted with ~22 mL of Normal Saline for a final concentration of 1 mg/mL [25 mg/25 mL]). Solutions were delivered to the patient using an operating suite using a sterile syringe. A total of 2 mL of omnipaque intravenous contrast was added into the mixture for radiopacity purposes under fluoroscopy and for in vivo visualization of the drug. Final concentration of the mixture was approximately 1 mg/mL. This mixture was agitated via a three-way stopcock in the absence of air.

The venous malformation was accessed percutaneously, using ultrasound and x-ray guidance. Intraluminal placement of the access needle was verified upon return of blood and confirmed by intralesional venography demonstrating the angioarchitecture of the targeted venous malformation. The prepared Temsirolimus emulsion was administered through direct intralesional delivery directly into the accessed venous malformation. Good deposition into the lesion, with some escape into the systemic circulation, was observed.

Different components of this focal venous malformation were similarly targeted and treated. 5 mL of Temsirolimus emulsion was deposited into the lesion. Serial x-rays revealed sustained presence of the emulsion inside the lesions with minimal escape.

Needle access tracts were plugged using a collagen matrix foam, and a sterile dressing was applied. The procedure was done under general endotracheal anesthesia, and the patient received postoperative anti-inflammatory and analgesic medications. The patient's post-operative labs were within expected, normal limits. The patient had no perioperative complications and was discharged home in stable condition.

Figure 5A:
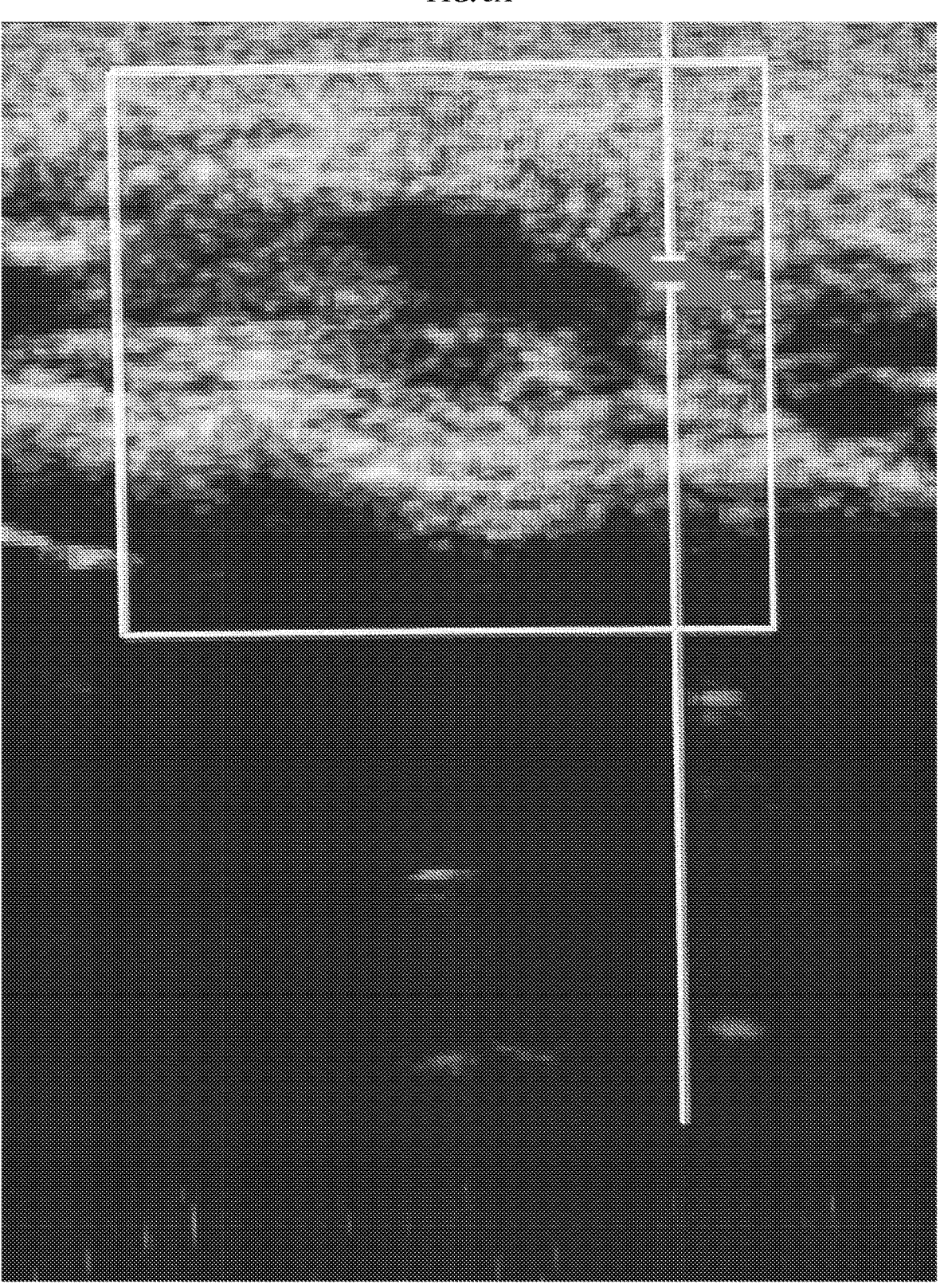
FIGS. 5A-5B illustrate color flow Doppler of a venous malformation following embolization with an mTOR inhibitor. There was cessation of venous flow within the malformation with preservation of normal arterial flow adjacent to the malformation. Preservation of this normal vessel, unrelated to the malformation, was confirmed by the demonstrated spectral waveform analysis demonstrating arterial pulsatility.
Figure 5B:
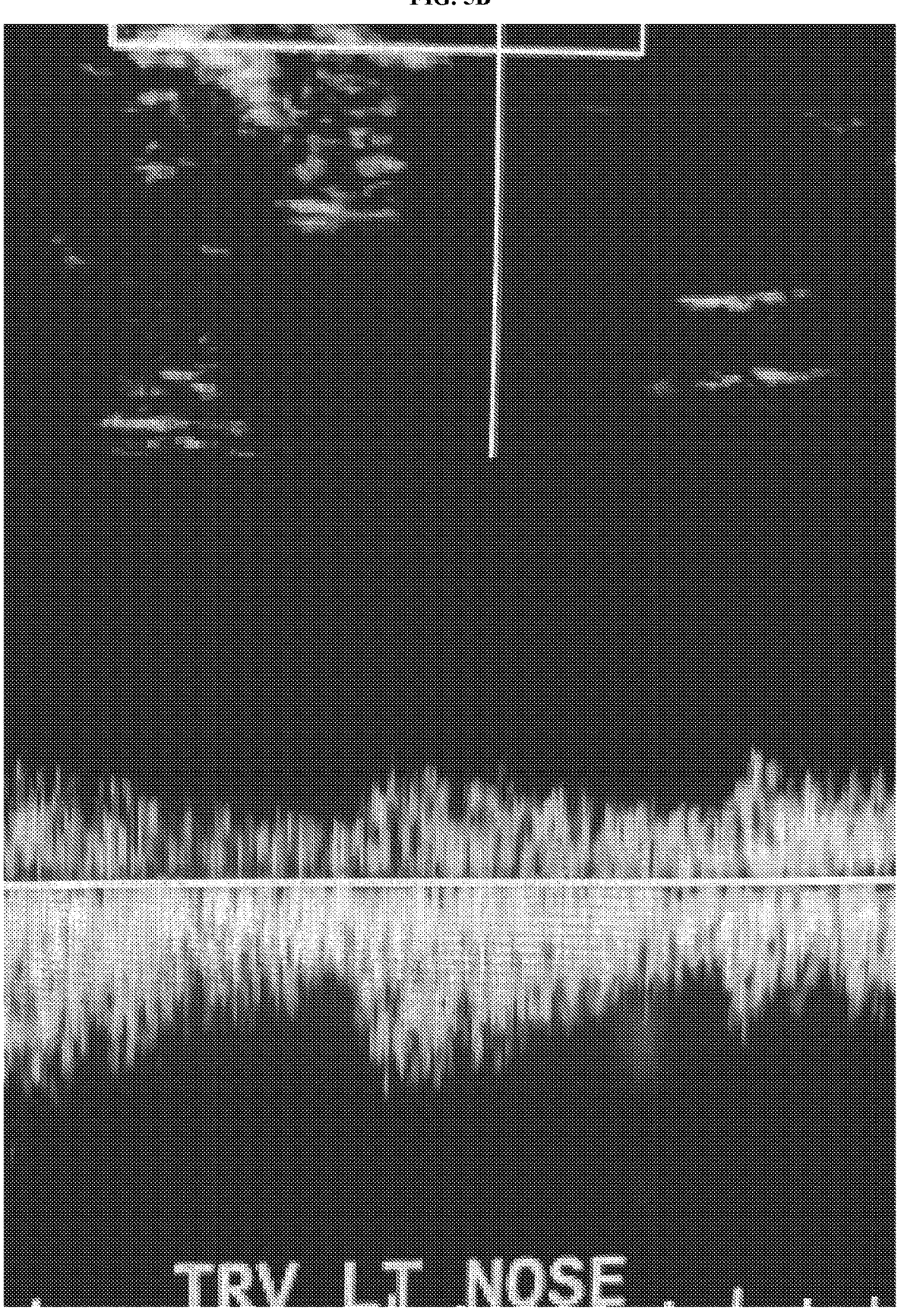
Figure 6A:
FIGS. 6A-6C illustrate non-limiting aspects of experiments described in Example 2.
Figure 6B:
Figure 6C:

On a follow-up interviews on post-operative day 14 and day ~90, the patient expressed partial pain relief and no evidence of fevers or infection. As illustrated in FIGS. 5A-5B, treatment of the second patient according to methods of the disclosure diminished venous flow in the left nasal venous malformation, with preservation of intervening normal arterial network of the face, as demonstrated by the pulsatility detected on spectral waveform analysis.

ENUMERATED EMBODIMENTS

The following exemplary embodiments are provided, the numbering of which is not to be construed as designating levels of importance:

Embodiment 1 provides a dose unit of a mTOR inhibitor, wherein the dose unit is sterile, wherein the mTOR is in a solution, or can be dissolved in a solvent to form a solution, and wherein the mTOR inhibitor concentration in the solution ranges from about 0.5 mg/ml to about 5 mg/ml.

Embodiment 2 provides the dose unit of Embodiment 1, wherein the mTOR inhibitor concentration in the solution is about 1 mg/ml.

Embodiment 3 provides the dose unit of any one of Embodiments 1-2, which is formulated in a solution comprising a diluent, saline, and a contrast dye.

Embodiment 4 provides the dose unit of any one of Embodiments 1-3, which is formulated as a solution with total volume ranging from about 5 ml to about 25 ml.

Embodiment 5 provides the dose unit of any one of Embodiments 1-4, which is formulated as a solution with total volume of about 10 ml.

Embodiment 6 provides the dose unit of any one of Embodiments 1-5, wherein the mTOR inhibitor is BEZ235, rapamycin, everolimus, AZD8055, Temsirolimus, KU-0063794, PI-103, Torkinib, Tacrolimus, Ridaforolimus, INK-128, Voxtalisib, Torin-1, Omipalisib, OSI-027, PF-04691502, Apitolisib, GSK1059615, WYE-354, Gedatolisib, AZD-2014, Torin-2, WYE-125132, BGT226, Palomid-529, PP121, WYE-687, CH5132799, Way-600, ETP-46464, GDC-0349, XL388, Zotarolimus, or a salt, solvate, enantiomer, or diastereoisomer thereof.

Embodiment 7 provides the dose unit of any one of Embodiments 1-6, wherein the mTOR inhibitor is at least one selected from the group consisting of rapamycin, Ridaforolimus, and Everolimus, or a salt, solvate, enantiomer, or diastereoisomer thereof.

Embodiment 8 provides the dose unit of any one of Embodiments 1-7, wherein the mTOR inhibitor is rapamycin, or a salt, solvate, enantiomer or diastereoisomer thereof.

Embodiment 9 provides the dose unit of any one of Embodiments 1-8, wherein the mTOR inhibitor is temsirolimus.

Embodiment 10 provides a method of treating at least one of a congenital vascular malformation, Klippel-Trenaunay syndrome, CLOVES syndrome, and Proteus syndrome in a subject, wherein the method comprises intralesionally administering to the subject a therapeutically effective amount of a mTOR inhibitor.

Embodiment 11 provides the method of Embodiment 10, wherein the mTOR inhibitor is the only therapeutically effective agent administered to the subject to treat or prevent the congenital vascular malformation.

Embodiment 12 provides the method of any one of Embodiments 10-11, wherein the method consists of intralesionally administering to the subject a therapeutically effective amount of a mTOR inhibitor.

Embodiment 13 provides the method of any one of Embodiments 10-12, wherein the congenital vascular malformation is venous.

Embodiment 14 provides the method of any one of Embodiments 10-12, wherein the congenital vascular malformation is lymphatic.

Embodiment 15 provides the method of any one of Embodiments 10-14, wherein the mTOR inhibitor is administered as the dose unit of claim 1.

Embodiment 16 provides the method of any one of Embodiments 10-15, wherein the mTOR inhibitor is BEZ235, rapamycin, everolimus, AZD8055, Temsirolimus, KU-0063794, PI-103, Torkinib, Tacrolimus, Ridaforolimus, INK-128, Voxtalisib, Torin-1, Omipalisib, OSI-027, PF-04691502, Apitolisib, GSK1059615, WYE-354, Gedatolisib, AZD-2014, Torin-2, WYE-125132, BGT226, Palomid-529, PP121, WYE-687, CH5132799, Way-600, ETP- 46464, GDC-0349, XL388, Zotarolimus, or a salt, solvate, enantiomer, or diastereoisomer thereof.

Embodiment 17 provides the method of any one of Embodiments 10-16, wherein the mTOR inhibitor is at least one selected from the group consisting of rapamycin, Ridaforolimus, and Everolimus, or a salt, solvate, enantiomer, or diastereoisomer thereof.

Embodiment 18 provides the method of any one of Embodiments 10-17, wherein the mTOR inhibitor is rapamycin, or a salt, solvate, enantiomer or diastereoisomer thereof. Embodiment 19 provides the method of any one of Embodiments 10-18, wherein the mTOR inhibitor is temsirolimus.

Embodiment 20 provides the method of any one of Embodiments 10-19, wherein the subject is a mammal.

Embodiment 21 provides the method of any one of Embodiments 10-20, wherein the subject is human.

The disclosures of each and every patent, patent application, and publication cited herein are hereby incorporated herein by reference in their entirety. While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed is:

1. A dose unit of a mTOR inhibitor,
wherein the dose unit is sterile,
wherein the dose unit comprises a contrast dye,
wherein the mTOR inhibitor is selected from the group consisting of BEZ235, everolimus, AZD8055, Temsirolimus, KU-0063794, PI-103, Torkinib, Tacrolimus, Ridaforolimus, INK-128, Voxtalisib, Torin-1, Omipalisib, OSI-027, PF-04691502, Apitolisib, GSK1059615, WYE-354, Gedatolisib, AZD-2014, Torin-2, WYE-125132, BGT226, Palomid-529, PP121, WYE-687, CH5132799, Way-600, ETP-46464, GDC-0349, XL388, and Zotarolimus, or a salt, solvate, enantiomer, or diastereoisomer thereof,
wherein the mTOR inhibitor is in a solution, or can be dissolved in a solvent to form a solution, and
wherein the mTOR inhibitor concentration in the solution ranges from about 0.5 mg/ml to about 5 mg/ml.

2. The dose unit of claim 1, wherein the mTOR inhibitor concentration in the solution is about 1 mg/ml.

3. The dose unit of claim 1, wherein the solution comprises at least one of a diluent and saline.

4. The dose unit of claim 1, which is formulated as a solution with total volume ranging from about 5 ml to about 25 ml.

5. The dose unit of claim 1, which is formulated as a solution with total volume of about 10 ml.

6. The dose unit of claim 1, wherein the mTOR inhibitor is at least one selected from the group consisting of Ridaforolimus and Everolimus, or a salt, solvate, enantiomer, or diastereoisomer thereof.

7. The dose unit of claim 1, wherein the mTOR inhibitor is temsirolimus, or a salt, solvate, enantiomer, or diastereoisomer thereof.

8. A method of treating or ameliorating at least one of a congenital vascular malformation, Klippel-Trenaunay syndrome, CLOVES syndrome, and Proteus syndrome in a subject,
wherein the method comprises intralesionally administering to the subject a therapeutically effective amount of a mTOR inhibitor,
wherein the mTOR inhibitor is selected from the group consisting of BEZ235, everolimus, AZD8055, Temsirolimus, KU-0063794, PI-103, Torkinib, Tacrolimus, Ridaforolimus, INK-128, Voxtalisib, Torin-1, Omipalisib, OSI-027, PF-04691502, Apitolisib, GSK1059615, WYE-354, Gedatolisib, AZD-2014, Torin-2, WYE-125132, BGT226, Palomid-529, PP121, WYE-687, CH5132799, Way-600, ETP-46464, GDC-0349, XL388, and Zotarolimus, or a salt, solvate, enantiomer, or diastereoisomer thereof.

9. The method of claim 8, wherein the mTOR inhibitor is the only therapeutically effective agent administered to the subject to treat or prevent the congenital vascular malformation.

10. The method of claim 8, wherein the mTOR inhibitor is administered as a sterile solution comprising a contrast dye, and wherein the mTOR inhibitor concentration in the solution ranges from about 0.5 mg/ml to about 5 mg/ml.

11. The method of claim 8, wherein the congenital vascular malformation is venous.

12. The method of claim 8, wherein the congenital vascular malformation is lymphatic.

13. The method of claim 8, wherein the mTOR inhibitor is at least one selected from the group consisting of Ridaforolimus and Everolimus, or a salt, solvate, enantiomer, or diastereoisomer thereof.

14. The method of claim 8, wherein the mTOR inhibitor is temsirolimus, or a salt, solvate, enantiomer, or diastereoisomer thereof.

15. The method of claim 8, wherein the subject is a mammal.

16. The dose unit of claim 1, wherein the contrast dye comprises oily contrast media.

17. The dose unit of claim 16, wherein the oily contrast medium is an ethiodized oil.

* * * * *